US011714029B2

(12) United States Patent
Al-Qasim et al.

(10) Patent No.: US 11,714,029 B2
(45) Date of Patent: Aug. 1, 2023

(54) CORE HOLDER FOR REAL-TIME MEASUREMENT AND VISUALIZATION

(71) Applicant: SAUDI ARABIAN OIL COMPANY, Dhahran (SA)

(72) Inventors: Abdulaziz S. Al-Qasim, Dhahran (SA); Amer Al-Anazi, Dhahran (SA); Taha Okasha, Dhahran (SA)

(73) Assignee: SAUDI ARABIAN OIL COMPANY, Dhahran (SA)

( * ) Notice: Subject to any disclaimer, the term of this patent is extended or adjusted under 35 U.S.C. 154(b) by 589 days.

(21) Appl. No.: 16/833,244

(22) Filed: Mar. 27, 2020

(65) Prior Publication Data

US 2021/0302280 A1 Sep. 30, 2021

(51) Int. Cl.
| G01N 1/08 | (2006.01) |
| G01N 1/31 | (2006.01) |
| G01K 11/32 | (2021.01) |
| G01L 11/02 | (2006.01) |
| E21B 49/02 | (2006.01) |

(52) U.S. Cl.
CPC ............... *G01N 1/08* (2013.01); *G01K 11/32* (2013.01); *G01L 11/025* (2013.01); *G01N 1/31* (2013.01); *E21B 49/02* (2013.01)

(58) Field of Classification Search
None
See application file for complete search history.

(56) References Cited

U.S. PATENT DOCUMENTS

| 4,798,805 A | 1/1989 | Issenmann |
| 5,412,581 A | 5/1995 | Tackett |
| 5,868,030 A | 2/1999 | Brumley et al. |
| 10,107,056 B2 | 10/2018 | Zhang et al. |
| (Continued) | | |

FOREIGN PATENT DOCUMENTS

| CN | 101701887 A | 5/2010 |
| CN | 109444092 A | 3/2019 |
| (Continued) | | |

OTHER PUBLICATIONS

Sun, Yankun et al., "Laboratory core flooding experimental systems for CO2 geosequestration: An updated review over the past decade", Journal of Rock Mechanics and Geotechnical Engineering, ScienceDirect, Elsevier B.V., vol. 8, Issue 1, Feb. 2016, pp. 113-126 (14 pages).

(Continued)

*Primary Examiner* — Daniel S Larkin
(74) *Attorney, Agent, or Firm* — Osha Bergman Watanabe & Burton LLP

(57) ABSTRACT

A core holder for core testing includes a body having a cavity. A sleeve is disposed within the cavity. The sleeve defines a chamber to hold one or more core plugs. One or more fiber-optic sensors are disposed at a perimeter of the chamber. Each fiber-optic sensor senses a parameter related to flow of fluid through the chamber. A core testing system includes one or more light sources to provide light to each fiber-optic sensor and one or more light detectors to detect light from each fiber-optic sensor. A method of core testing may include injecting a fluid into one or more core plugs inside the chamber and measuring one or more parameters related to flow of fluid through the one or more core plugs.

13 Claims, 13 Drawing Sheets

(56) References Cited

U.S. PATENT DOCUMENTS

| | | | |
|---|---|---|---|
| 10,184,904 B1 | 1/2019 | Gong et al. | |
| 10,844,711 B2 * | 11/2020 | Cooper | E21B 49/02 |
| 2015/0004714 A1 | 1/2015 | Hanby | |
| 2016/0298445 A1 * | 10/2016 | Al-Khalifa | G01F 1/66 |
| 2018/0292477 A1 | 10/2018 | Chen et al. | |
| 2019/0162644 A1 | 5/2019 | Fadhel et al. | |

FOREIGN PATENT DOCUMENTS

| | | | |
|---|---|---|---|
| CN | 109653741 A | 4/2019 | |
| CN | 109855974 A | 6/2019 | |
| CN | 110487634 | * 11/2019 | G01N 27/041 |
| CN | 110700822 A | 1/2020 | |
| RU | 157556 U1 | 12/2015 | |
| WO | WO-2016146989 A1 * | 9/2016 | |
| WO | 2017010977 A1 | 1/2017 | |

OTHER PUBLICATIONS

International Search Report issued in corresponding International Application No. PCT/US2020/031595, dated Jan. 22, 2021 (4 pages).

Written Opinion issued in corresponding International Application No. PCT/US2020/031595, dated Jan. 22, 2021 (8 pages).

* cited by examiner

CORE HOLDER FOR REAL-TIME MEASUREMENT AND VISUALIZATION

BACKGROUND

Core testing is used in the oil and gas industry to investigate various properties of a reservoir, such as porosity, permeability, and fluid saturation. Before performing a core test, one or more core plugs have to be prepared. Typically, this involves taking a cylindrical rock sample from a side of an oil or gas well using a core bit. The rock sample is then cut into multiple pieces, each of which forms a core plug. To conduct a core flooding test, for example, a core plug is commonly placed inside a polymeric sleeve inside a pressurized core holder. The core plug may be saturated with oil and water to simulate real reservoir conditions. The temperature and pressure conditions in the core holder are set to mimic reservoir conditions. While the core plug is under pressure, fluid is pumped through the core plug. The pressure drop and flow rate across the core plug are measured and used to determine various flow properties of the core plug.

In conventional core holders, it is typically not possible to see what is happening inside the core holder in real time without use of complicated machines, such as an x-ray tomography machine. Moreover, conventional core holders do not generally allow for continuous real-time monitoring of parameters, such as temperature, across the core plug.

SUMMARY

A core holder for core testing includes a body having a cavity defined therein; a sleeve disposed within the cavity; a chamber defined within the sleeve, the chamber to hold at least one core plug; and at least one fiber-optic sensor disposed at a perimeter of the chamber, the at least one fiber-optic sensor to sense at least one parameter related to flow of fluid through the chamber. At least a portion of a wall of the body may be made of a transparent material to allow visual monitoring of a condition within the cavity. At least a portion of the sleeve may be made of a transparent material to allow visual monitoring of a condition with the chamber. The at least one fiber-optic sensor may include an optical fiber having a sensing region. The optical fiber may be carried by the sleeve. The at least one fiber-optic sensor may be a fiber-optic temperature sensor, a fiber-optic pressure sensor, or a fiber-optic pressure and temperature sensor. The core holder may include a seal member disposed within the sleeve and positioned to form a barrier between the at least one fiber-optic sensor and the chamber. The core holder may include a first plug disposed at an inlet end of the body. The first plug has a port to permit fluid communication with the cavity from an exterior of the core holder. The core holder may include a second plug disposed at an end of the sleeve proximate the inlet end of the body. The second plug may have a second port aligned for fluid communication with the first port. The core holder may include a plurality of fiber-optic sensors. Each fiber-optic sensor may include an optical fiber having a sensing region. The optical fibers of the plurality of optical fibers may be arranged in parallel on an inner surface of the sleeve. The core holder may include a plurality of fiber-optic sensor. Alternatively, the optical fibers of the plurality of fiber-optic sensors may be arranged to form a loop pattern on an inner surface of the sleeve. An annular space may be defined between the sleeve and the body to hold fluid around the sleeve. The core holder may include at least one port connected to feed fluid into the annular space.

A core testing system includes a core holder having a chamber to hold at least one core plug and at least one fiber-optic sensor disposed at a perimeter of the chamber to sense at least one parameter related to flow of fluid through the chamber; at least one light source connected to the at least one fiber-optic sensor; and at least one light detector connected to the at least one fiber-optic sensor. The core holder may include a body having cavity. The chamber may be defined within the cavity. At least a portion of the body of the core holder may be made of a transparent material. The core holder may include a sleeve disposed inside the cavity. The chamber may be defined within the sleeve. At least a portion of the sleeve may be made of a transparent material. The at least one fiber-optic sensor may be carried by the sleeve. The at least one fiber-optic sensor may be a fiber-optic temperature sensor, a fiber-optic pressure sensor, or a fiber-optic pressure and temperature sensor. The core holder may include a seal member disposed within the sleeve and positioned to form a barrier between the at least one fiber-optic sensor and the chamber. The core testing system may include a pump that is in fluid communication with the chamber.

A method of core testing includes placing at least one core plug within a chamber defined within a core holder; positioning at least one fiber-optic sensor within the core holder and at a perimeter of the chamber; injecting a fluid into the at least one core plug within the chamber; and measuring, with the at least one fiber-optic sensor, at least one parameter related to flow of the fluid through the at least one core plug. Measuring at least one parameter related to the flow of the fluid through the at least one core plug may include measuring changes in a temperature in an environment of the at least one core plug by the at least one fiber-optic sensor. Measuring at least one parameter related to the flow of the fluid through the at least one core plug may include measuring changes in pressure in an environment of the at least one core plug by the at least one fiber-optic sensor.

The foregoing general description and the following detailed description are exemplary of the invention and are intended to provide an overview or framework for understanding the nature of the invention as it is claimed. The accompanying drawings are included to provide further understanding of the invention and are incorporated in and constitute a part of the specification. The drawings illustrate various embodiments of the invention and together with the description serve to explain the principles and operation of the invention.

BRIEF DESCRIPTION OF DRAWINGS

The following is a description of the figures in the accompanying drawings. In the drawings, identical reference numbers identify similar elements or acts. The sizes and relative positions of elements in the drawings are not necessarily drawn to scale. For example, the shapes of various elements and angles are not necessarily drawn to scale, and some of these elements may be arbitrarily enlarged and positioned to improve drawing legibility. Further, the particular shapes of the elements as drawn are not necessarily intended to convey any information regarding the actual shape of the particular elements and have been solely selected for ease of recognition in the drawing.

DETAILED DESCRIPTION

Figure 1:
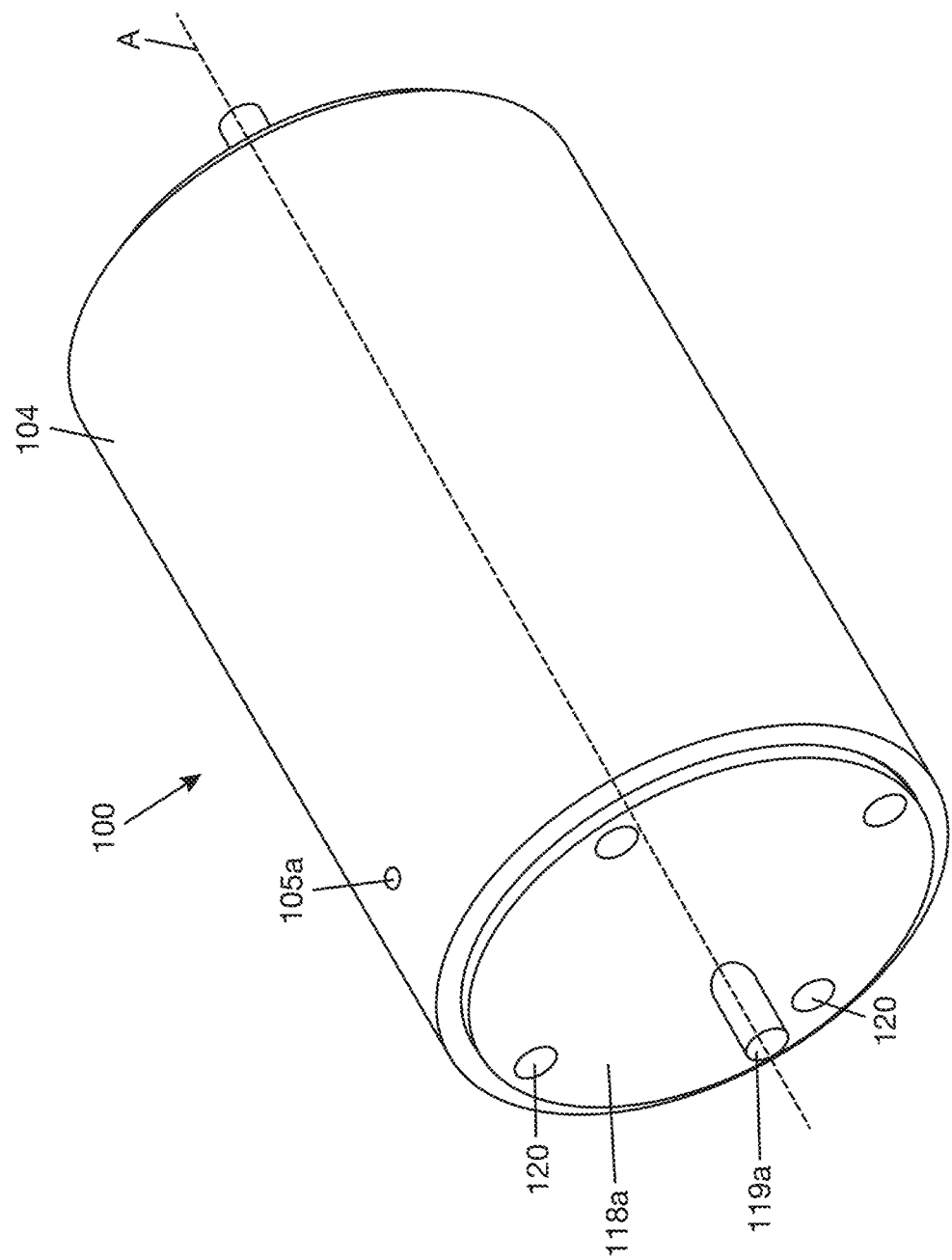
FIG. 1 is a perspective view of a core holder.
Figure 2:
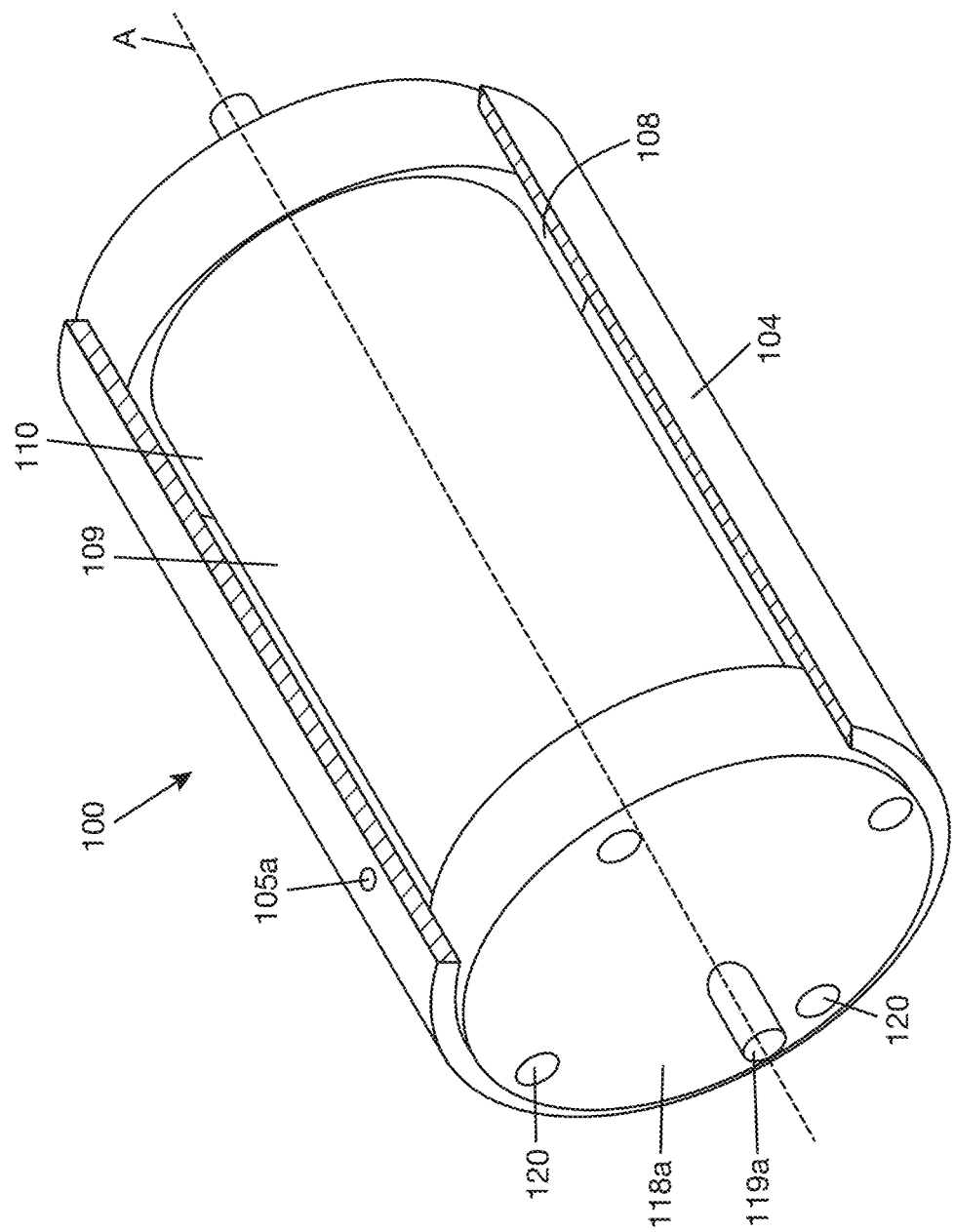
FIG. 2 is a cutaway view of the core holder shown in FIG. 1.

In the following detailed description, certain specific details are set forth in order to provide a thorough understanding of various disclosed implementations and embodiments. However, one skilled in the relevant art will recognize that implementations and embodiments may be practiced without one or more of these specific details, or with other methods, components, materials, and so forth. In other instances, well known features or processes have not been shown or described in detail to avoid unnecessarily obscuring descriptions of the implementations and embodiments. For the sake of continuity, and in the interest of conciseness, same or similar reference characters may be used for same or similar objects in multiple figures.

Embodiments disclosed herein relate to simulating flooding experiments in, for example, the oil and gas industry, to obtain fluid and flow properties. More specifically, embodiments disclosed herein relate to integrating the use of fiber optics technology with a core holder for simulating flooding experiments to determine fluid permeability and flow properties.

It is to be further understood that the various embodiments described herein may be used in various stages of core testing to analyze and measure core plug properties, such as simulating flooding experiments in the oil and gas industry to obtain fluid permeability and flow properties, chemical analysis, hydrocarbon saturation, grain density etc., and in other industries, such as construction and the study of geology. Flooding experiments may refer to core flood testing that may mimic reservoir conditions (i.e., pressure and temperature) on a core plug. For example, a pressure or flow of fluid may be applied across or through the core plug that corresponds to a similar pressure or flow experienced by rock in a reservoir. Initially, the core plug may be disposed in a simulated formation brine, oil, or combination of brine and oil at the start of the core flood test. Fluids, such as crude oil, simulated reservoir brine, drilling muds, acids, and/or other chemicals, may then be injected into the core holder while various measurements of the core and fluid are recorded. Core flood tests recorded measurements and results may then be used to guide mathematical models and extract critical simulation parameters for well operations.

Figure 3:
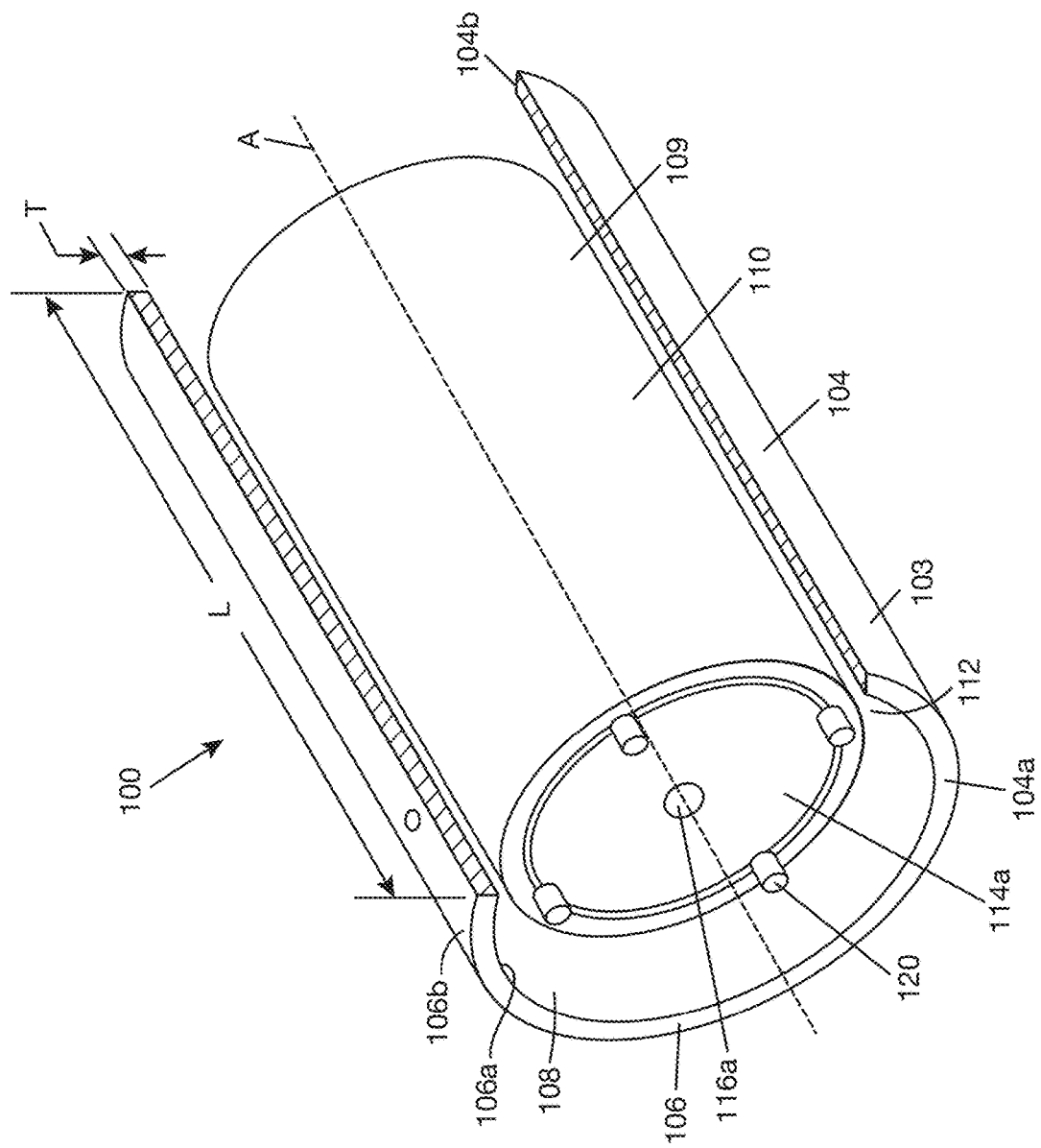
FIG. 3 shows the core holder of FIG. 1 with outer end plugs removed to allow viewing of the interior of the core holder.
Figure 4:
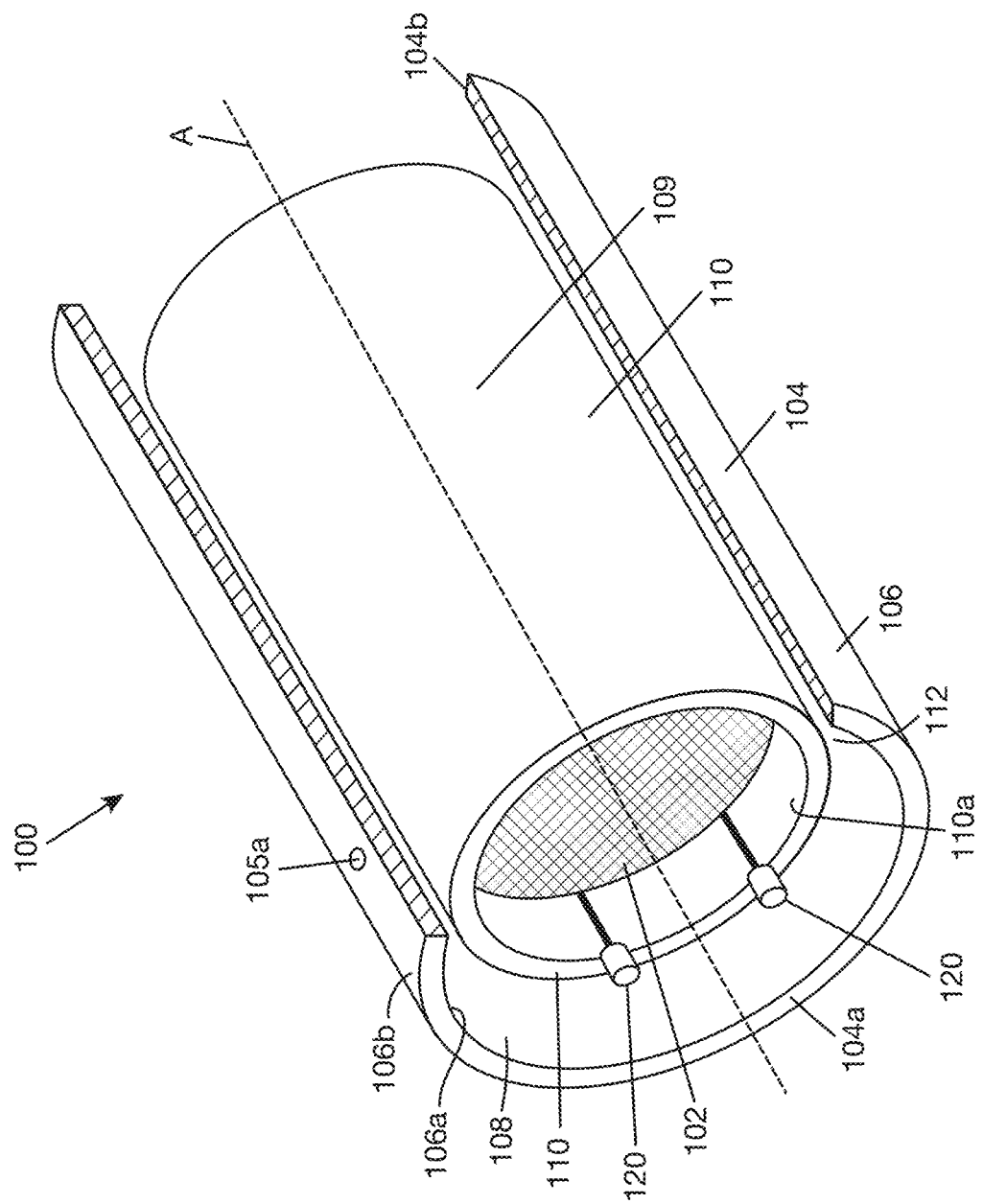
FIG. 4 shows the core holder of FIG. 3 with inner end plugs removed from an inner core holder to allow viewing of a core plug inside the inner core holder.
Figure 6:
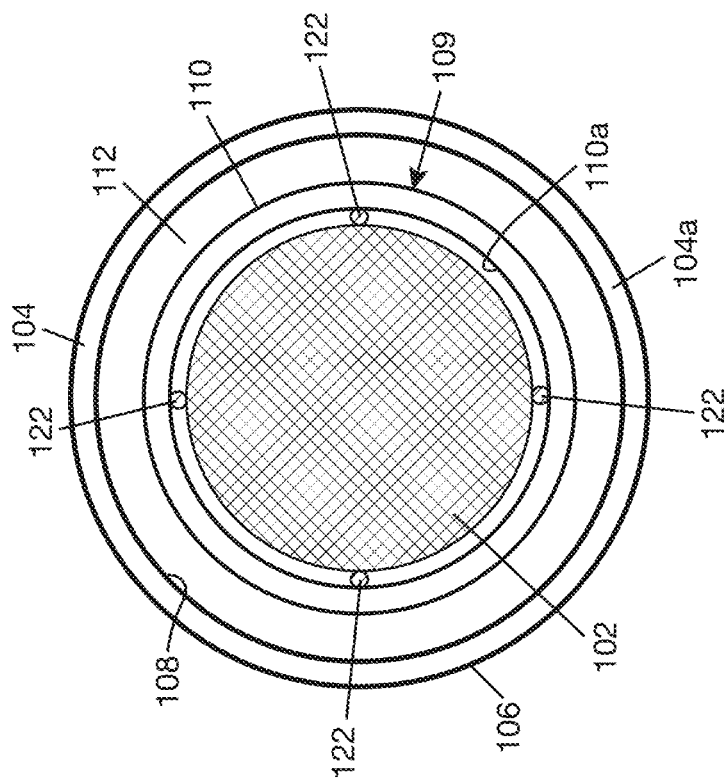
FIG. 6 is an end view of the core holder shown in FIG. 4.
Figure 5:
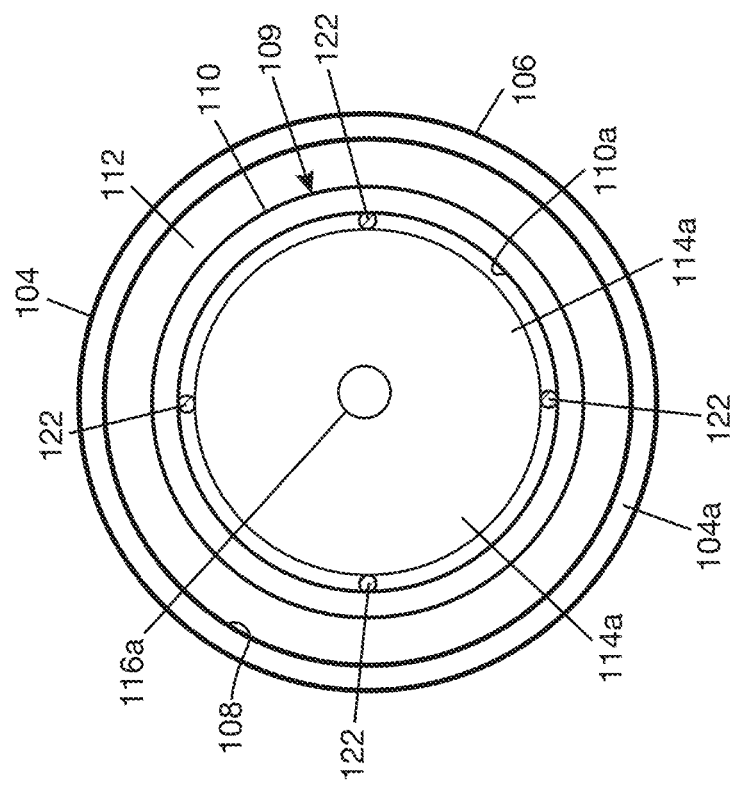
FIG. 5 is an end view of the core holder shown in FIG. 3.
Figure 7:
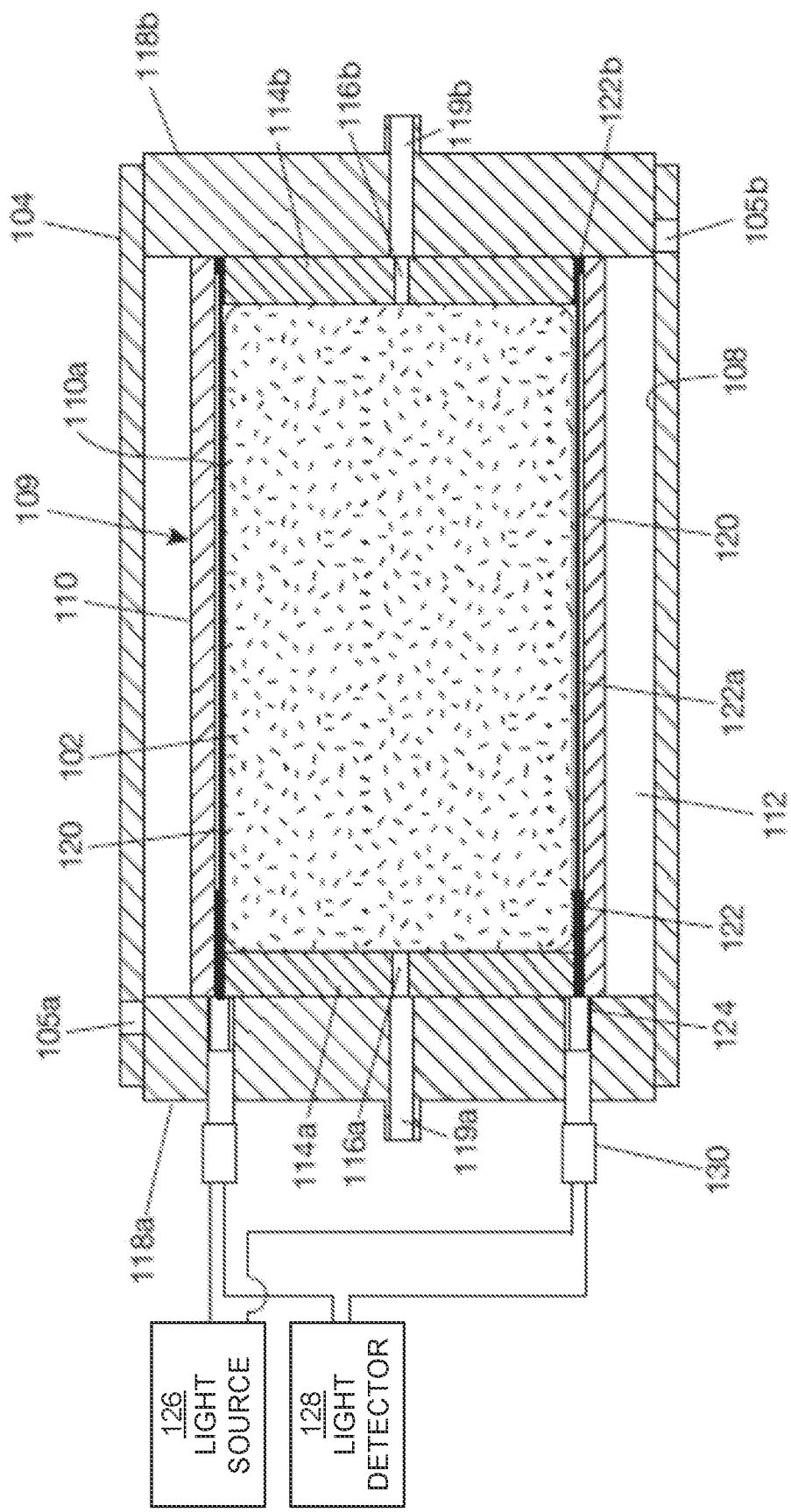
FIG. 7 is a cross-sectional view of the core holder of FIG. 1 with fiber-optic sensors coupled to a light source and a light detector in reflection mode.
Figure 8:
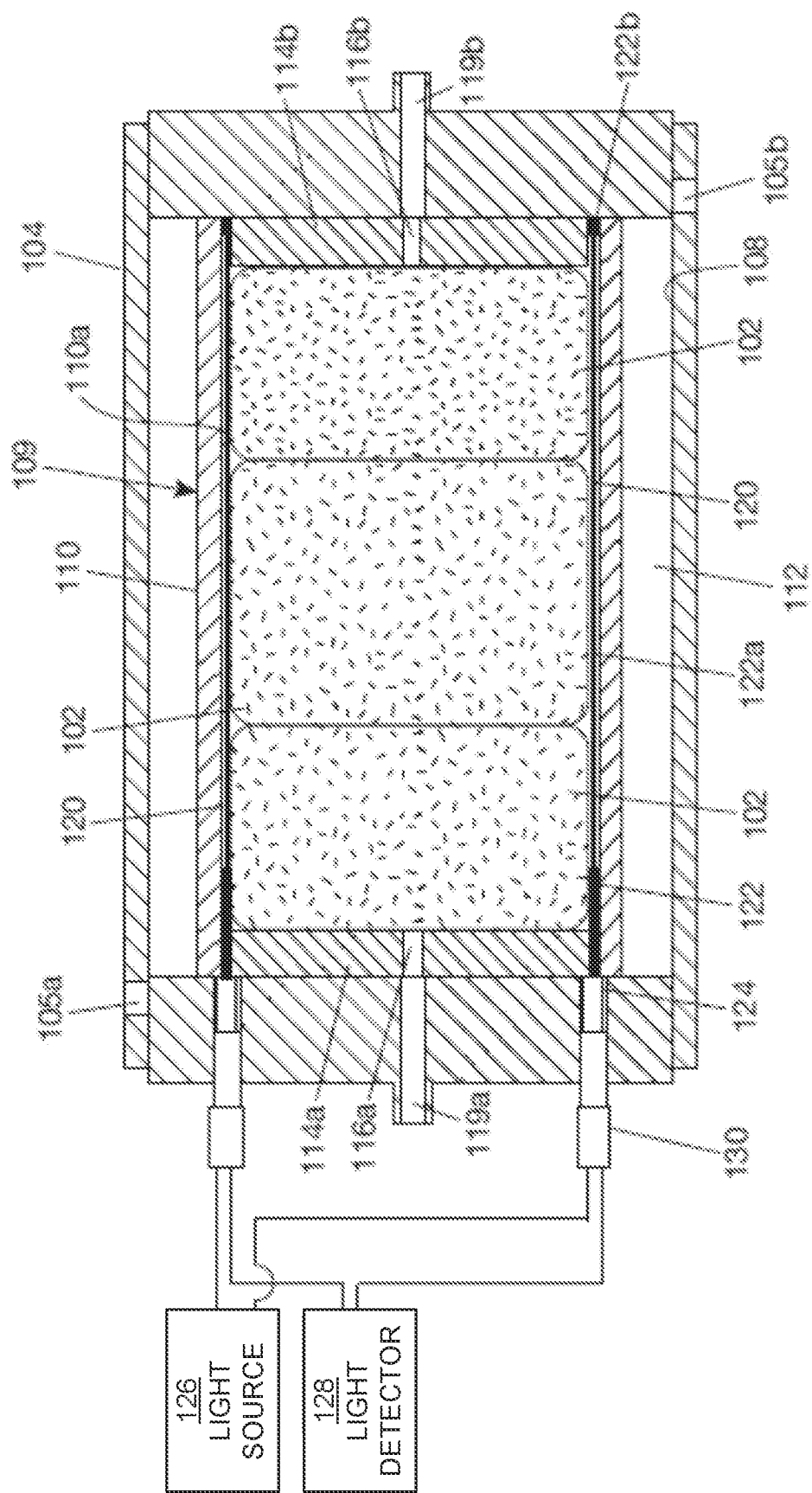
FIG. 8 is a cross-sectional view of the core holder of FIG. 1 showing multiple core plugs within a sleeve inside the core holder.

FIGS. 1-8 show various views of a core holder 100 in accordance with one or more embodiments. Core holder 100 may hold one or more core plugs for testing. The term "core plug" will generally refer to a porous body in the general shape of a cylinder. In the oil and gas field, core plugs may be obtained from a rock sample taken from the side of a drilled oil or gas well using a core bit. For illustration purposes, FIGS. 4, 6, and 7 show a core plug 102 within core holder 100. For completeness, FIG. 8 shows that multiple core plugs 102 of various lengths may be within core holder 100 in other implementations. For core testing, core holder 100 may be coupled to testing equipment (not shown). As an example, the testing equipment may include a pump that is operable to inject fluid into core plug(s) 102 within core holder 100. The rate and pressure at which fluid is injected into core plug(s) 102 may be selected to simulate flooding of a reservoir. In addition, the testing equipment may include or be connected to a computer system (not shown) to store, calculate, and display results from various tests using core holder 100.

Core holder 100 has a body 104 with an axial axis A (in FIGS. 1-4). In FIGS. 1-8, body 104 has a hollow cylindrical shape. However, body 104 is not limited to this shape. For example, body 104 may have a tubular shape with other types of cross-sections, such as oval cross-section or rectangular cross-section or square cross-section. As illustrated in FIG. 3, body 104 has a wall 106 with length L and thickness T. Wall 106 extends from a first end surface 104a of body 104 to a second end surface 104b of body 104. Wall 106 defines a cavity 108 to hold core plug(s) 102. Length L of wall 106 may be selected based on a length (or lengths) of core plug(s) 102 (in FIGS. 4, 6, 7, and 8) to be disposed within core holder 100 for testing. For example, if a core plug of some given length is to be arranged inside core holder 100, length L of wall 106 should be at least as long as the length of the core plug. In another example, if multiple core plugs are to be arranged in series inside core holder 100, as shown in FIG. 8, then length L should be long enough to accommodate the combined length of the multiple core plugs. Similarly, the diameter of cavity 108 (or inner diameter of wall 106) may be selected based on the outer diameter of core plug(s) 102 to be disposed within core holder 100 for testing.

In one or more embodiments, wall 106 may be made from a transparent material to allow visual monitoring of the interior of core holder 100. The material of wall 106 may be, for example, glass, plastic, gypsum plaster, or other transparent and high-temperature-resistant material. The material of wall 106 may be reinforced or strengthened. In some cases, a transparent window may be formed in wall 106 rather than forming the entire wall 106 with a transparent material. Transparency of at least a portion of wall 106 may allow visual monitoring of flow within cavity 108 and core plug(s) 102 during testing of core plug(s) 102. For example, testing of core plug(s) 102 may involve applying heat to core plug(s) 102. In this case, the effect of heat on core plug(s) 102 may be visually monitored from outside core holder 100. The material and/or thickness T of wall 106 are preferably selected to allow wall 106 to withstand pressures and temperatures that would be encountered during testing of core plug(s) 102.

Pressure taps 105a, 105b may be formed in wall 106. Pressure gauges (not shown) may be connected to pressure taps 105a, 105b to measure pressure within core holder 100. In other cases, other sensors (not shown) may be embedded in wall 106 for other types of measurements within cavity 108. These other sensors may include, for example, temperature sensors, which may allow measurement of temperatures at the boundaries of the core plug(s) 102. The measured temperatures may be used to determine temperature across the core plug(s) 102 and used to adjust heat input to the system.

In one implementation, an inner core holder 109 (in FIGS. 2-8) is disposed inside cavity 108. Inner core holder 109 extends generally in the same direction as axial axis A of body 104. The length of the inner core holder 109 along axial axis A may be selected to be shorter than length L of wall 106 of body 104 so that inner core holder 109 can be fully contained inside cavity 108 formed by wall 106. Although one inner core holder 109 is shown within wall 106, it is possible to have multiple inner core holders 109 in other implementations. In some cases, the multiple inner core holders 109 may be arranged in series inside cavity 108. In this case, the combined length of the multiple core holders 109 is preferably shorter than length L of wall 106 of body 104 so that the multiple inner core holders can be fully contained inside cavity 108.

In one implementation, inner core holder 109 includes a sleeve 110 having an inner surface 110a that defines a chamber to hold one or more core plug(s) 102. Sleeve 110 may be coaxial with wall 106. Sleeve 110 may be made of a polymeric material or other conformable (or flexible) material. In some cases, the material of sleeve 110 may be waterproof. Examples of materials that may be used for sleeve 110 include, but are not limited to, fluorocarbon-based synthetic rubber, polyvinyl chloride (PVC), and flexible gypsum material. Sleeve 110 has a size and shape to hold one or more core plugs 102. To allow visual monitoring of the core plug(s) 102 within sleeve 110, sleeve 110 may be made of transparent material or have a transparent window. The material of sleeve 110 may be reinforced.

In one implementation, inner core holder 109 includes inner end plugs 114a, 114b (in FIGS. 3, 5, 7, and 8), which are disposed at opposite ends of sleeve 110. Alternatively, it is possible to provide inner end plugs 114a, 114b as end caps. Inner end plugs 114a, 114b include ports (e.g., through-holes) 116a, 116b (in FIGS. 3, 5, 7, and 8), respectively, to allow fluid communication with the interior of sleeve 110 and core plug(s) 102.

Outer end plugs 118a, 118b (in FIGS. 1, 2, 7, and 8) may be disposed at opposite ends of body 104 of core holder 100. Alternatively, it is possible to provide outer end plugs 118a, 118b as end caps. The end of body 104 where outer end plug 118a is disposed may be the inlet end of core holder 100, and the body 104 where outer end plug 118a is disposed may be the outlet end. The terms "inlet" and "outlet" are relative to where fluid enters cavity 108 and where fluid exits cavity 108, respectively. Outer end plugs 118a, 118b have ports 119a, 119b, which may be aligned with ports 116a, 116b, respectively, in inner end plugs 114a, 114b. For core testing, a fluid source (not shown) may be connected to port 119a, and a fluid drain (not shown) may be connected to port 119b, which would allow fluid to be circulated through core plug(s) 102 within inner core holder 109.

In one implementation, sleeve 110 (or inner core holder 109) is radially spaced from inner surface 106a of wall 106 such that an annular space 112 is formed between sleeve 110 (or inner core holder 109) and wall 106. Fluid may be supplied into annular space 112 to pressurize core holder 100 and support sleeve 110 within cavity 108. Flow dynamics in annular space 112 may be studied to validate fluid behavior in many drilling activities. For example, while injecting a fluid into a formation, the pressure in the annulus is critical to designing certain injection schema. This can be simulated in core testing by structuring the fluid in annular space 112 to apply hydrostatic pressure around sleeve 110 at the same pressure value that would be expected during drilling activities. In some cases, wall 106 may include a first port (not shown) through which fluid can be supplied into annular space 112 and a second port (not shown) to allow air to escape from annular space 112 while filling annular space 112 with fluid. Alternatively, ports (121a, 121b in FIG. 7) may be formed in outer end plugs 118a, 118b to allow annular space 112 to be filled with fluid.

In one implementation, inner core holder 109 includes or carries one or more fiber-optic sensors 120 (in FIGS. 3-8). In one implementation, fiber-optic sensor(s) 120 are arranged within inner core holder 109 such that they are positioned at a perimeter of a chamber defined within inner core holder 109 to hold core plug(s) 102. In general, each fiber-optic sensor 120 may be any fiber-optic sensor 120 capable of sensing and detecting a desired stimulus in an environment in which the sensor is disposed. In one example, at least one of fiber-optic sensors 120 may be a fiber-optic temperature sensor. In another example, at least one of fiber-optic sensors 120 may be a fiber-optic pressure sensor. In yet another example, at least one of fiber-optic sensors 120 may be a fiber-optic pressure and temperature sensor. In some implementations, an array of fiber-optic sensors 120 measuring the same stimulus may be carried by inner core holder 109. In other implementations, an array of fiber-optic sensors 120 measuring different stimuli may be carried by inner core holder 109.

Figure 9:
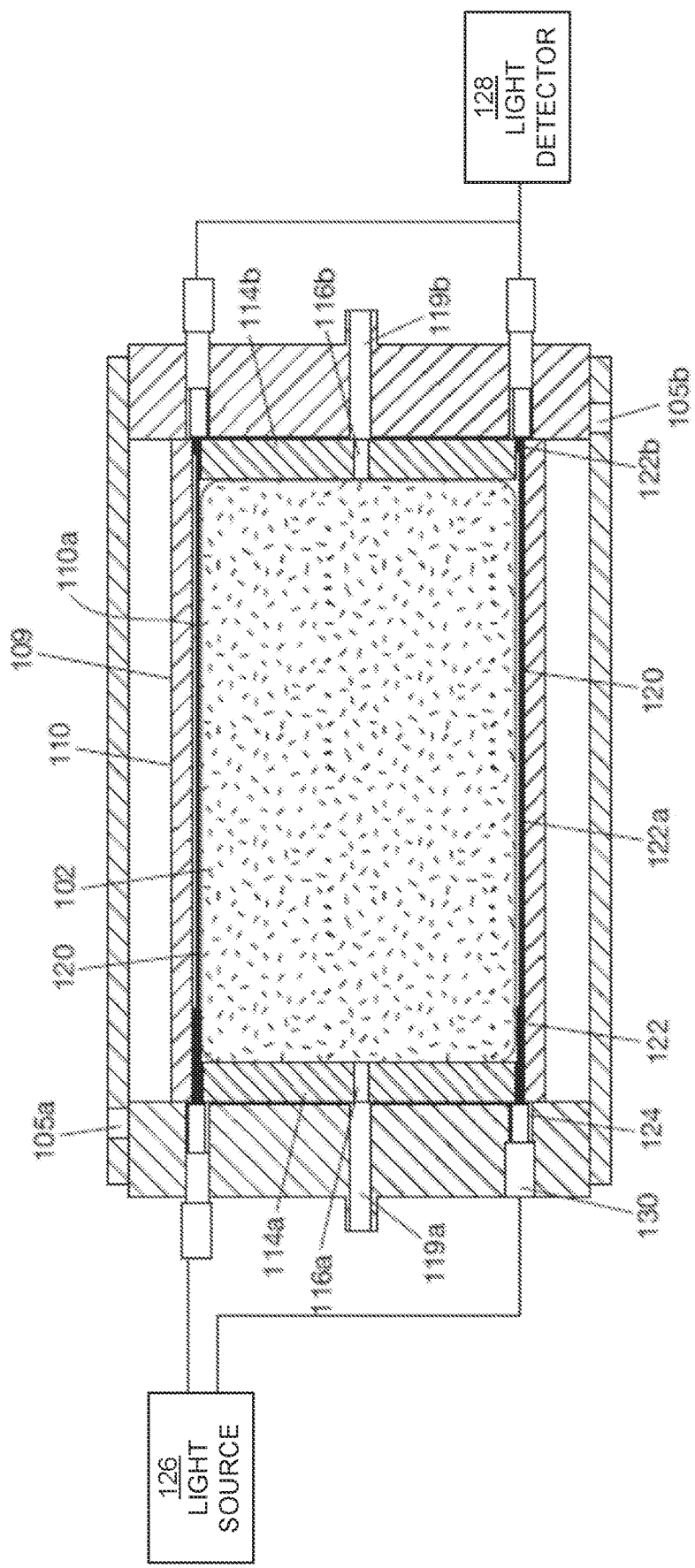
FIG. 9 is a cross-sectional view of a core holder with fiber-optic sensors coupled to a light source and a light detector in transmission mode.

Referring to FIG. 7, as an example, fiber-optic sensor 120 may include an optical fiber 122 with a sensing region 122a. Sensing region 122a may be made of a material (or have a structure) that is sensitive to a desired stimulus in the environment (or chamber) defined within sleeve 110. For example, sensing region 122a may be sensitive to temperature or pressure or other desired stimulus. In some cases, sensing region 122a may be sensitive to more than one stimuli, e.g., both temperature and pressure. Other stimuli that sensing region 122a may be selectively sensitive to include, but are not limited to, pressure drop, fluid viscosity, fluid density, and acidity or alkalinity. In the illustrated example, optical fiber 122 is inserted in a ferrule 124. In an example where fiber-optic sensor 120 is operating in a reflection mode, ferrule 124 may be connected to a light source 126, e.g., a laser source, and light detector 128 through a connector 130. In this example, light source 126 will generate light that is transmitted to sensing region 122a of optical fiber 122. The light will be modified by changes in sensing region 122a due to interaction of sensing region 122a with the environment. The modified light will be reflected back to light detector 128 through optical fiber 122 and connector 130. In some implementations, end 122b of optical fiber 122 may be shaped or include a coating material or include a lens function to back-reflect light into optical fiber 122. Alternatively, as illustrated in FIG. 9, fiber-optic sensor 120 may be configured to operate in a transmission mode, where the modified light from sensing region 122a is detected by detector 128 through end 122b of optical fiber 122.

Figure 10:
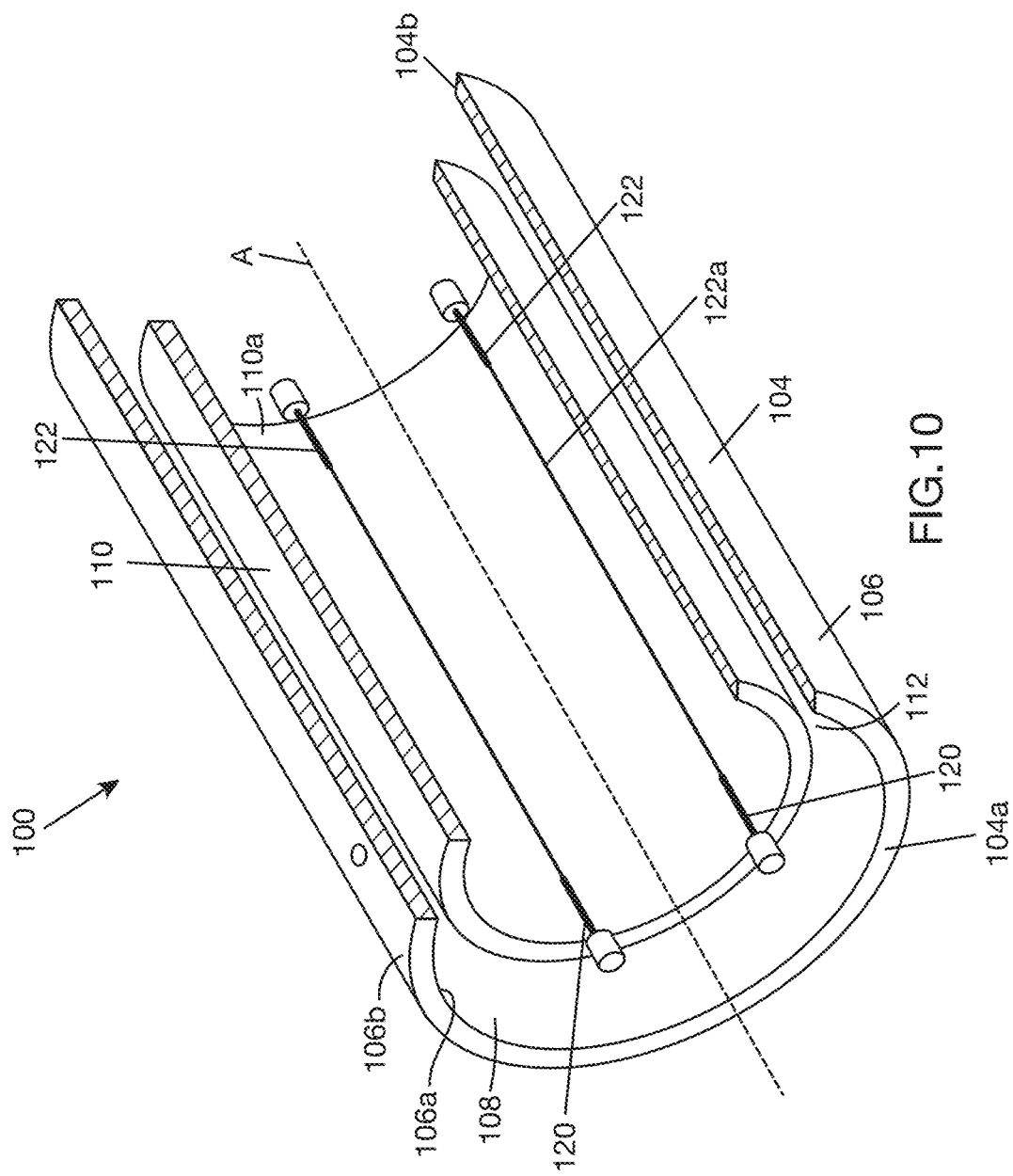
FIG. 10 shows the core holder of FIG. 4 with the sleeve cut away and the core plug removed to allow viewing of optical fibers carried by the sleeve.
Figure 11:
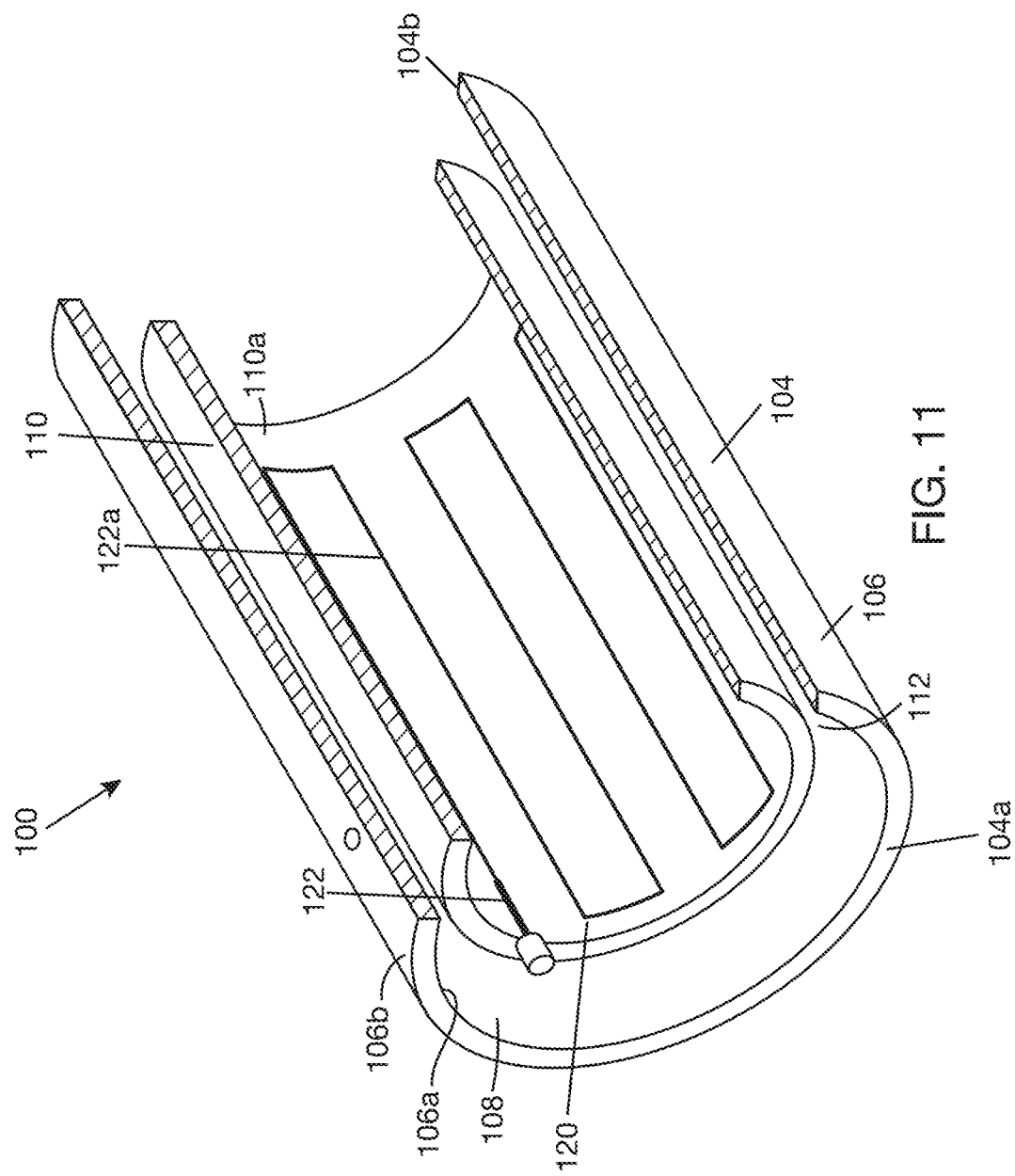
FIG. 11 shows the core holder of FIG. 10 with an optical fiber arranged in a multiple-loop pattern on an inner surface of the sleeve.
Figure 12:
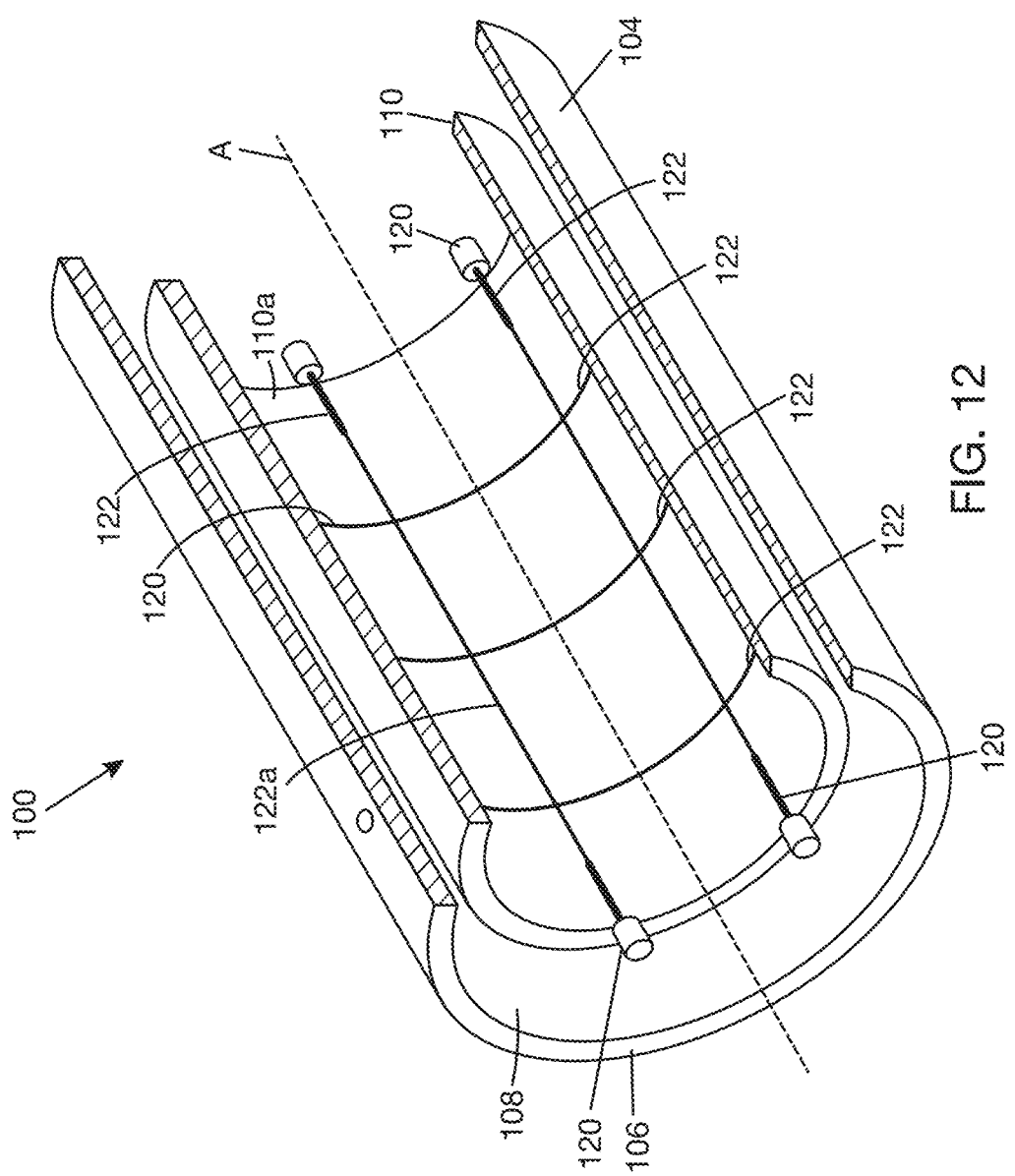
FIG. 12 shows the core holder of FIG. 10 with optical fibers arranged in a grid pattern on an inner surface of the sleeve.

In one implementation, optical fiber(s) 122 of fiber-optic sensor(s) 120 may be carried by, e.g., attached to or embedded in, inner surface 110a of sleeve 110, which would place optical fiber(s) 122 at a perimeter of the chamber defined by inner surface 110a of sleeve 110. For illustrative purposes, FIG. 10 shows optical fibers 122 carried by inner surface 110a of sleeve 110. The number of optical fibers 122 (or number of fiber-optic sensors 120) carried by inner surface 110a of sleeve 110 may be determined by the desired resolution of the measurements. In one example, optical fibers 122 may be arranged in parallel and spaced-apart relation along a circumference of inner surface 110a of sleeve, with a length of each optical fiber 122 oriented along a length of sleeve 110 or along axial axis A, as shown in FIG. 10. In some implementations, optical fiber 122 of fiber-optic sensor 120 may be arranged to form a single loop pattern or multiple-loop pattern or spiral pattern on inner surface 110a. The loop or spiral pattern allows greater coverage of the inner surface 110a with a single continuous optical fiber. FIG. 11 shows an example of optical fiber 122 (or sensing region 122a of optical fiber 122) arranged to form a multiple-loop pattern. The multiple-loop pattern may continue along the entire circumference of inner surface 110a or may be formed in just a portion of the circumference of inner surface 110a. In the case of a spiral pattern, this may resemble forming a thread on inner surface 110a. In other implementations, optical fibers 122 may be arranged to form a grid pattern on inner surface 110a, as illustrated in FIG. 12. The grid pattern may include some of the optical fibers 122 extending along a length of sleeve 110 and others of the optical fibers 122 extending along an inner circumference of sleeve 110.

Fiber optic sensor(s) 120 provide core holder 100 with the capability to measure and monitor changes in various conditions within sleeve 110, such as pressure and temperature, continuously on real-time basis while testing core plug(s) 102. In some embodiments, measurements taken from fiber-optic sensor(s) 120 may provide useful diagnostic indicators for analysis of fluid flow within core plug(s) 102 and for identifying in-situ flow, pore connectivity, and other flow parameters on a real-time basis. In one example, fiber-optic sensor(s) 120 may be temperature sensors that monitor temperature across core plug 102. Flow rate changes across core plug 102 may be inferred from the temperature measurements made by fiber-optic sensor(s) 120.

Figure 13:
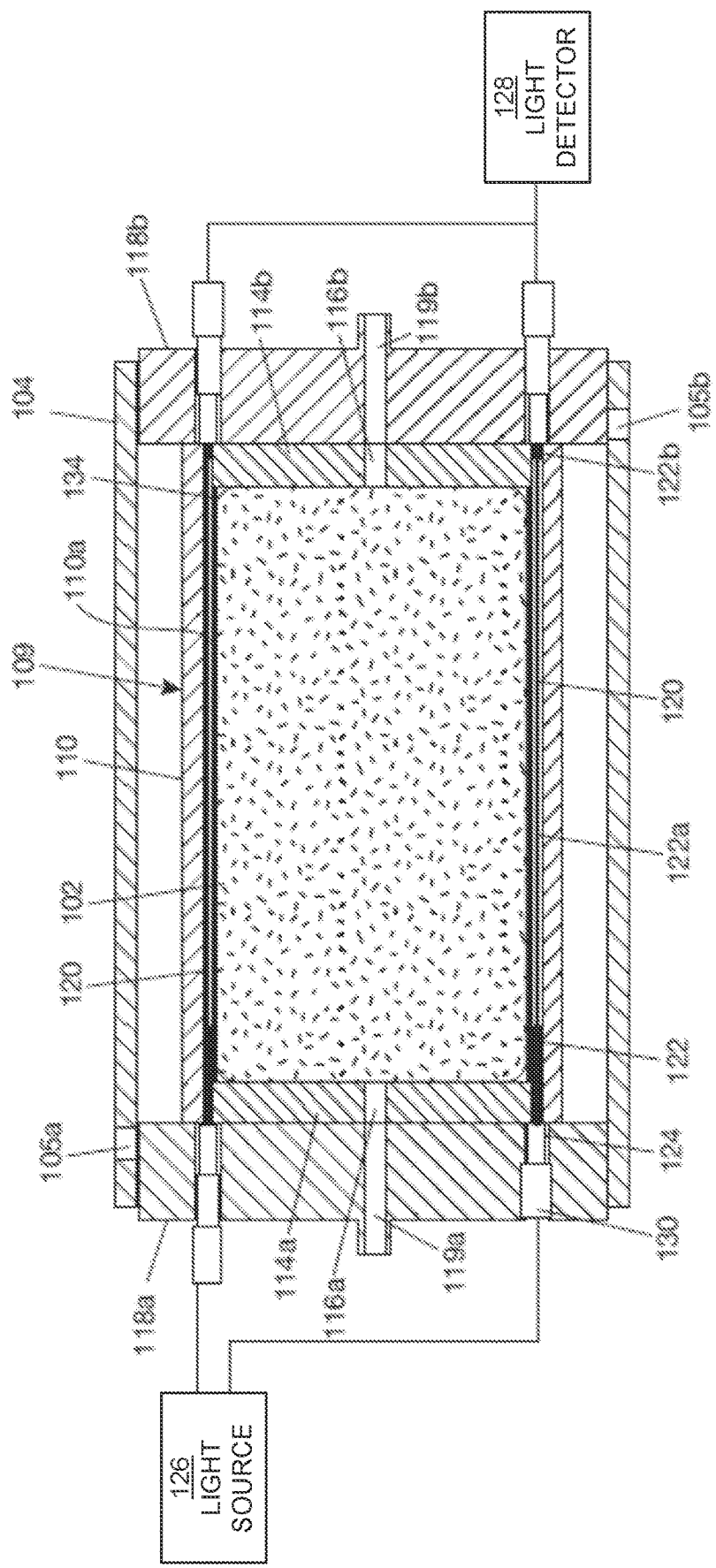
FIG. 13 is an alternative cross-sectional view of the core holder of FIG. 9 showing a seal member between a core plug and fiber-optic sensors.

Referring to FIG. 13, inner core holder 109 may include a seal member 134 that is disposed between core plug(s) 102 and optical fiber(s) 122 of fiber optic sensor(s) 120 to prevent direct contact between optical fiber(s) 122 and core plug(s) 102. Seal member 134 may have a generally cylindrical shape or other shape to hold one or more core plug(s) 102. In this case, the chamber to hold core plug(s) 102 is now located within seal member 134. Seal member 134 may be made of any suitable sealing material. Alternatively, optical fiber(s) 122 may be encapsulated in a protective sleeve or bag, such as a polymeric sleeve or bag, which would also serve the function of isolating optical fiber(s) 122 from core plug(s) 102.

Figure 14:
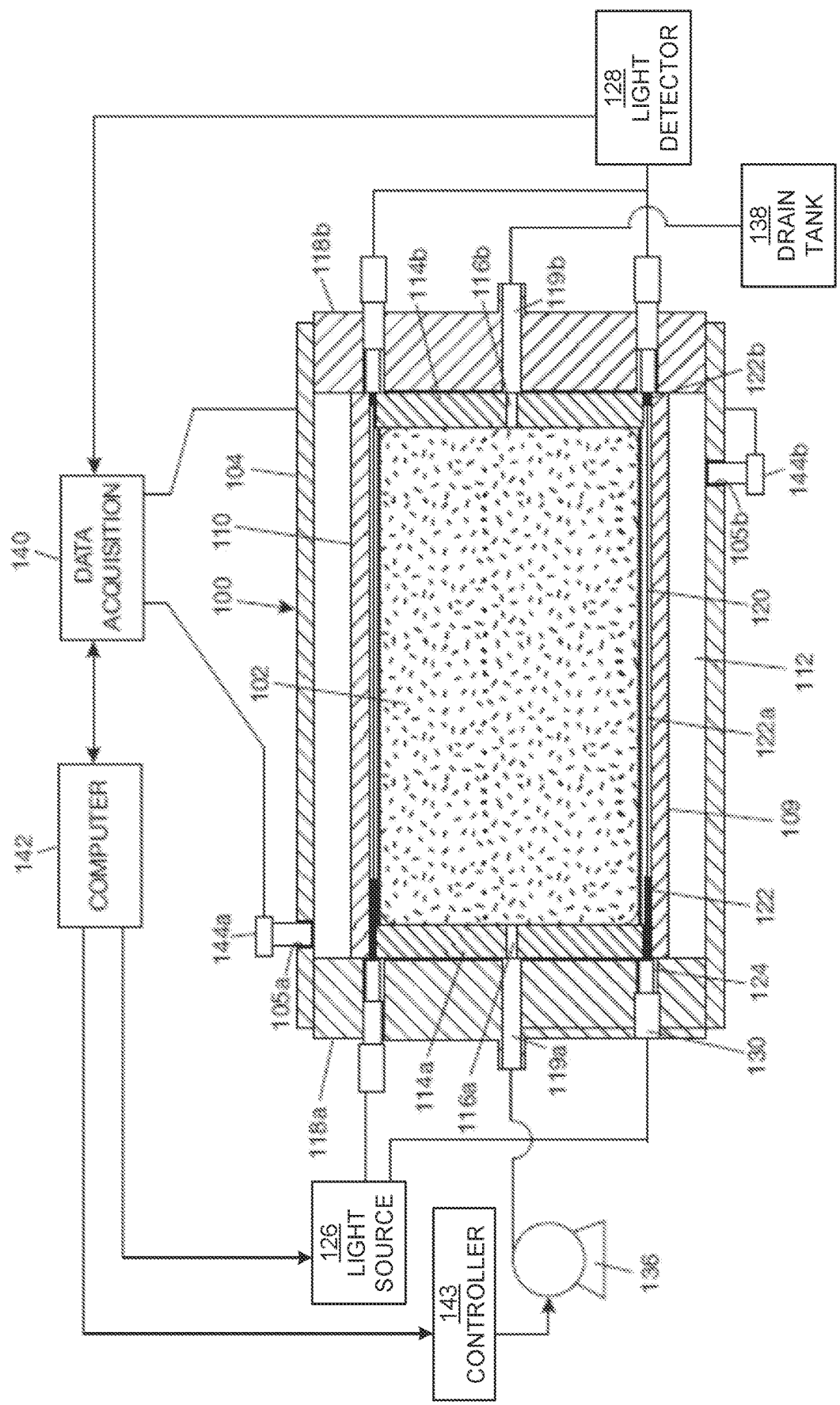
FIG. 14 shows an example core testing setup with the core holder shown in FIG. 9.

FIG. 14 shows an example core testing setup with core holder 100. In the setup, core plug 102 is disposed inside inner core holder 109, which is disposed inside core holder 100. Core plug 102 may be a piece of a rock sample taken from a side of a drilled oil or gas well. The discharge end of a pump 136 is connected to port 119a in outer end plug 118a. Port 119b in outer end plug 118b may be connected to a drain tank 138. Fiber optic sensor(s) 120 are connected to light source 126 and light detector 128. In addition, light detector 128 is connected to data acquisition system 140, which may be in communication with a computer system 142. Core testing may be initiated and controlled from an interface on computer system 142. FIG. 14 shows, for example, that a controller 143 for pump 136 and a driver (not shown separately) for light source 126 may receive control signals from computer system 142. Pressure gauges 144a, 144b may be connected to (or inserted into) pressure taps 105a, 105b. Pressure gauges 144a, 144b may be connected to data acquisition system 140. Prior to conducting testing, annular space 112 may be filled with pressurized fluid.

To use the setup in FIG. 14 for core testing, fluid may be injected into core plug 102 by pump 136. The fluid injection can be continuous over a desired measurement period. During this measurement period, the temperature of core plug 102 (or other stimulus in the environment of core plug 102) can be monitored by fiber optic sensor(s) 120. The sensing region 122a of optical fiber 122 of fiber-optic sensor 120 will modulate light passing through optical fiber 122 as the temperature (or other stimulus) in the environment changes. Light detector 128 will detect light from optical fiber 122 and generate a signal that is representative of a characteristic of the detected light, e.g., the intensity of the detected light. Data acquisition system 140 receives the output of light detector 128 and may process the output. Computer system 142 may retrieve the output of light detector 128 (as well as other data such as output of pressure gauges 144a, 144b) from data acquisition system 140 and use the output in computation of various flow parameters related to core plug 102.

Benefits of the core testing system using core holder 100 may include the capability to monitor changes in flow rate within the core plug, estimate water saturation within the core plug, monitor real-time saturation, pressure, and temperature within the core plug, monitor preferred path of water, oil, and gases through the core plug, help in perforation design, provide better estimation for permeability continuous profile, and provide better assessment for enhanced oil recovery (EOR) process and water shut-off jobs. Water saturation can be estimated via measuring the weight of the core plug and the volume of liquid injected into the core plug and produced (i.e., conduct volumetric analysis and material balance of initial and final conditions). This can be supported by sensing changes in pressure drop across the core plug. If necessary, the system can be equipped with advanced logging techniques that can measure resistivity and calculate water saturation using Archie equation. Nuclear magnetic resonance (NMR) is also one of the common logging techniques that can be deployed with the system to measure saturations, measure permeability/porosity profiles, and capture real-time fluid movements inside the core plug.

While the invention has been described with respect to a limited number of embodiments, those skilled in the art, having the benefit of this disclosure, will appreciate that other embodiments can be devised that do not depart from the scope of the invention as described herein. Accordingly, the scope of the invention should be limited only by the accompanying claims.

The invention claimed is:

1. A core holder for core testing, the core holder comprising:
   a body having a cavity defined therein;
   a sleeve disposed within the cavity;

a chamber defined within the sleeve, the chamber to hold at least one core plug; and at least one fiber-optic sensor disposed at a perimeter of the chamber, the at least one fiber-optic sensor to sense at least one parameter related to flow of fluid through the chamber, wherein the at least one fiber-optic sensor comprises an optical fiber having a sensing region extending along an axial direction of the core holder, and wherein the optical fiber is attached to or embedded in an inner surface of the sleeve, wherein the at least one fiber-optic sensor is a fiber-optic temperature sensor, a fiber-optic pressure sensor, or a fiber-optic pressure and temperature sensor, and wherein at least a portion of a wall of the body is made of a transparent material to allow visual monitoring of a condition within the cavity.

2. The core holder of claim 1, further comprising a seal member disposed within the sleeve and positioned to form a barrier between the at least one fiber-optic sensor and the chamber.

3. The core holder of claim 1, further comprising a first plug disposed at an inlet end of the body, the first plug having a first port to permit fluid communication with the cavity from an exterior of the core holder.

4. The core holder of claim 3, further comprising a second plug disposed at an end of the sleeve proximate the inlet end of the body, the second plug having a second port aligned for fluid communication with the first port.

5. The core holder of claim 1, which comprises a plurality of fiber-optic sensors, each fiber-optic sensor comprising an optical fiber having a sensing region, wherein the optical fibers of the plurality of fiber-optic sensors are arranged in parallel on an inner surface of the sleeve.

6. The core holder of claim 1, which comprises a plurality of fiber-optic sensors, each fiber-optic sensor comprising an optical fiber having a sensing region, wherein the optical fibers of the plurality of fiber-optic sensors are arranged to form a grid pattern or a loop pattern on an inner surface of the sleeve.

7. The core holder of claim 1, wherein an annular space is defined between the sleeve and the body to hold fluid around the sleeve.

8. A core testing system comprising:
a core holder having a chamber to hold at least one core plug and at least one fiber-optic sensor disposed at a perimeter of the chamber to sense at least one parameter related to flow of fluid through the chamber;

at least one light source connected to the at least one fiber-optic sensor; and at least one light detector connected to the at least one fiber-optic sensor, wherein the core holder comprises a body having a cavity and a sleeve disposed inside the cavity, and wherein the chamber is defined within the sleeve, wherein the at least one fiber-optic sensor comprises an optical fiber having a sensing region extending along an axial direction of the core holder, and wherein the optical fiber is attached to or embedded in an inner surface of the sleeve, wherein the at least one fiber-optic sensor is a fiber-optic temperature sensor, a fiber-optic pressure sensor, or a fiber-optic pressure and temperature sensor, and wherein at least a portion of a wall of the body is made of a transparent material to allow visual monitoring of a condition within the cavity.

9. The core testing system of claim 8, wherein the core holder comprises a seal member disposed within the sleeve and positioned to form a barrier between the at least one fiber-optic sensor and the chamber.

10. The core testing system of claim 8, further comprising a pump in fluid communication with the chamber.

11. A method of core testing, the method comprising:
placing at least one core plug within a chamber defined within a core holder;

the core holder comprising a body having a cavity and a sleeve disposed inside the cavity, the chamber being defined within the sleeve;

positioning at least one fiber-optic sensor within the core holder and at a perimeter of the chamber;

the at least one fiber-optic sensor comprising an optical fiber having a sensing region extending along an axial direction of the core holder, wherein the optical fiber is attached to or embedded in an inner surface of the sleeve, the at least one fiber-optic sensor being a fiber-optic temperature sensor, a fiber-optic pressure sensor, or a fiber-optic pressure and temperature sensor at least a portion of a wall of the body being made of a transparent material to allow visual monitoring of a condition within the cavity;

injecting a fluid into the at least one core plug within the chamber; and measuring, with the at least one fiber-optic sensor, at least one parameter related to flow of the fluid through the at least one core plug.

12. The method of claim 11, wherein measuring, with the at least one fiber-optic sensor, at least one parameter related to flow of the fluid through the core plug comprises measuring changes in a temperature in an environment of the at least one core plug by the at least one fiber-optic sensor.

13. The method of claim 11, wherein measuring, with the at least one fiber-optic sensor, at least one parameter related to flow of the fluid through the core plug comprises measuring changes in a pressure in an environment of the at least one core plug by the at least one fiber-optic sensor.

* * * * *